(12) United States Patent  (10) Patent No.: US 8,042,389 B2
Sprung  (45) Date of Patent: Oct. 25, 2011

(54) ADJUSTABLE HYDROMETER

(76) Inventor: Julian Sprung, Miami Beach, FL (US)

( * ) Notice: Subject to any disclaimer, the term of this patent is extended or adjusted under 35 U.S.C. 154(b) by 398 days.

(21) Appl. No.: 12/432,640

(22) Filed: Apr. 29, 2009

(65) Prior Publication Data

US 2009/0266159 A1 Oct. 29, 2009

Related U.S. Application Data

(60) Provisional application No. 61/071,442, filed on Apr. 29, 2008, provisional application No. 61/104,844, filed on Oct. 13, 2008.

(51) Int. Cl.
*G01N 9/00* (2006.01)
(52) U.S. Cl. .................. 73/454; 73/434; 73/451; 73/433
(58) Field of Classification Search .................... 73/434, 73/451, 454, 433
See application file for complete search history.

(56) References Cited

U.S. PATENT DOCUMENTS

| 3,722,292 | A | * | 3/1973 | Pietramale | 73/454 |
| 6,776,040 | B2 | * | 8/2004 | Wong | 73/454 |
| 2002/0194912 | A1 | * | 12/2002 | Tu | 73/454 |

* cited by examiner

*Primary Examiner* — Lisa Caputo
*Assistant Examiner* — Jamel Williams
(74) *Attorney, Agent, or Firm* — Venable LLP; Michael A. Gollin; Ryan M. Flandro

(57) ABSTRACT

A hydrometer, hydrometer kit, and method of measuring the salinity/density or the salinity/specific gravity of a liquid are provided. The hydrometer may include a box structure comprising side walls and a bottom. At least a portion of one of the side walls may be substantially transparent. A buoyant indicator member may be pivotably disposed about an axis within the box structure. The indicator member may pivot about the axis when the box structure is filled with a liquid. A salinity/density scale or salinity/specific gravity scale may be disposed on a surface of the box structure or a dial member. At least one adhesive member may be removably adhered to the indicator member by a user so that the hydrometer can be calibrated based on a reference solution having a predetermined salinity. The at least one adhesive member may increase or decrease the buoyancy of the indicator member. The kit may include the hydrometer and a container of the reference solution having a predetermined salinity.

11 Claims, 11 Drawing Sheets

ADJUSTABLE HYDROMETER

CROSS-REFERENCE TO RELATED APPLICATIONS

This application claims priority benefit under 35 U.S.C. §119(e) of U.S. Provisional Application No. 61/071,442, filed Apr. 29, 2008, the entirety of which is hereby incorporated by reference. This application also claims priority benefit under 35 U.S.C. §119(e) of U.S. Provisional Application No. 61/104,844, filed Oct. 13, 2008, the entirety of which is hereby incorporated by reference.

BACKGROUND

1. Field of Invention

The invention is related to hydrometers and, more particularly, to box-style (box-type), swing-arm hydrometers used for measuring the concentration of dissolved salts in natural or artificial seawater.

2. Related Art

Hydrometers are instruments used to measure the density or specific gravity (also commonly referred to as relative density) of a liquid, i.e., the density of the liquid as compared to that of water when both are at the same temperature. Substances with a specific gravity greater than one are denser than water (and so will sink in it), and those with a specific gravity of less than one are less dense than water (and so will float in it). Hydrometers are often used, for example, by marine or brackish water aquarium enthusiasts who use natural or artificial seawater in their aquariums, or by people conducting field analysis of natural seawater.

Many types of seawater density measuring devices exist but generally may fall under three categories: (1) conductivity meters, which measure dissolved salts electronically; (2) refractometers, which measure density or salinity indirectly by passing light through the sample, using the refraction index of a liquid which is proportional to the amount of dissolved substances in the liquid; and (3) hydrometers, which come in several forms, but typically have some type of float that gives an indication of the water density based on a fixed scale. Each of these measuring devices must be calibrated for a specific temperature range, and each has its own advantages and disadvantages. Conductivity meters, for example, can be expensive, delicate instruments that need to be well maintained. They can also be difficult to operate correctly without proper training and, therefore, are generally not practical for use by the average aquarium hobbyist. Refractometers can be more practical, but require good eyesight and the reading must be taken quickly because evaporation of the sample can give inaccurate readings in a short period of time. Both conductivity meters and refractometers have a negative attribute in that they can be damaged by the effects of saltwater causing corrosion of metal parts.

Hydrometers are generally the most practical devices for use by aquarium hobbyists. Known hydrometers are typically sold as a device that has been calibrated and checked by the manufacturer. Thus, the user relies on the precision of the manufacturing for the level of accuracy and cannot calibrate the device manually. Several different types of hydrometers are known. One type of hydrometer, for example, includes a calibrated glass or plastic tube ending in a weighted portion that makes the tube stand upright when placed in a liquid. The lower the density of the liquid, the deeper the tube sinks. This type of hydrometer may typically contain a paper scale positioned inside the stem so that the specific gravity can be read directly based on the point at which the surface of the liquid touches the stem of the hydrometer. Such glass or plastic float hydrometers may be sufficiently accurate for aquarium hobby use, but it can be difficult to determine the correct reading because of the meniscus at the stem and the necessarily tiny print on the scale. Glass or plastic float hydrometers must also be calibrated by the manufacturer within a narrow temperature range, otherwise the readings will be off. Accurate glass or plastic float hydrometers can also be expensive and those made of glass may also be easily broken.

Another common type of hydrometer known in the aquarium trade is the box-style, swing-arm hydrometer. Box-style, swing-arm hydrometers are popular because they are easy to read, easy to use, and are relatively inexpensive. These hydrometers may typically include three components: (1) a box or tube; (2) an indicator arm (pointer) disposed in the box or tube and which points to numbers on a fixed scale; and (3) a counter weight disposed within the pointer. Differences in the dimensions of the box and/or the pointer as well as slight variations in the weight of the counter weight can all impact the accuracy of the hydrometer. Also, deposits of minerals on the pointer can make the accuracy change over time. Furthermore, if air bubbles become attached to the pointer as the hydrometer is being filled, the reading may not be accurate. Thus, although box-style, swing-arm hydrometers are generally designed to give fairly accurate readings across a wide range of temperature (called "temperature compensation"), they can have numerous disadvantages.

SUMMARY

In an embodiment of the invention, a hydrometer is provided. The hydrometer may be a box-style (box-type), swing-arm hydrometer and may include a box structure comprising side walls and a bottom. At least a portion of one of the side walls may be substantially transparent. A buoyant indicator member may be pivotably disposed about an axis within the box structure. The indicator member may pivot about the axis when the box structure is filled with a liquid. A salinity/density scale or salinity/specific gravity scale may be disposed on a surface of the box structure or a dial member. At least one adhesive member may be adapted to be removably adhered to the indicator member by a user so that the hydrometer can be calibrated based on a reference solution having a predetermined salinity. The at least one adhesive member may increase or decrease the buoyancy of the indicator member.

In an embodiment of the invention, the buoyant indicator member may be removable.

In an embodiment of the invention, the salinity/density scale or salinity/specific gravity scale may be adjustable or fixed relative to the box structure.

In another embodiment of the invention, a kit may be provided. The kit may include the hydrometer and a container containing a reference solution having a predetermined salinity.

In yet another embodiment of the invention, a hydrometer may be provided. The hydrometer may include means for containing a liquid and means for indicating the salinity/density or the salinity/specific gravity of the liquid contained in said liquid containing means. The indicating means may be adjustable relative to the liquid containing means so that the hydrometer can be calibrated based on a reference solution having a predetermined salinity.

In still another embodiment, a method of measuring the salinity/density or the salinity/specific gravity of a liquid may be provided. The method may include providing a hydrometer. The hydrometer may include a box structure comprising side walls and a bottom, wherein at least a portion of one of the side walls is substantially transparent; a buoyant indicator member pivotably disposed about an axis within the box structure; and a salinity/density or salinity/specific gravity scale disposed on a surface of the box structure or a dial member. The method may further include providing at least one adhesive member adapted to be removably adhered to the indicator member by a user so that the hydrometer can be calibrated based on a reference solution having a predetermined salinity. The at least one adhesive member may be configured to increase or decrease the buoyancy of the indicator member. The method may include filling the hydrometer with a reference solution having a predetermined salinity. The method may include calibrating the hydrometer by adhering the at least one adhesive member to the indicator member as necessary such that the indicator member indicates the predetermined salinity of the reference solution on the scale. The method may include removing the reference solution from the box structure and filling the calibrated hydrometer with the liquid to be measured. The method may include measuring the salinity/density or the salinity/specific gravity of the liquid by reading the salinity/density or the salinity/specific gravity indicated on the scale by the buoyant indicator member.

Further features and advantages of the invention, as well as the structure and operation of various embodiments of the invention, are described in detail below with reference to the accompanying drawings.

BRIEF DESCRIPTION OF THE DRAWINGS

The foregoing and other features and advantages of the invention will be apparent from the following, more particular description of embodiments of the invention, as illustrated in the accompanying drawings wherein like reference numbers generally indicate identical, functionally similar, and/or structurally similar elements. Unless otherwise indicated, the accompanying drawing figures are not to scale. The dimensions shown in any of FIGS. 1-12d are example dimensions according to an embodiment of the invention and one of ordinary skill will recognize that such dimensions could be modified as necessary based on different sizes, designs, and applications of the hydrometer.

DETAILED DESCRIPTION

Figure 2:
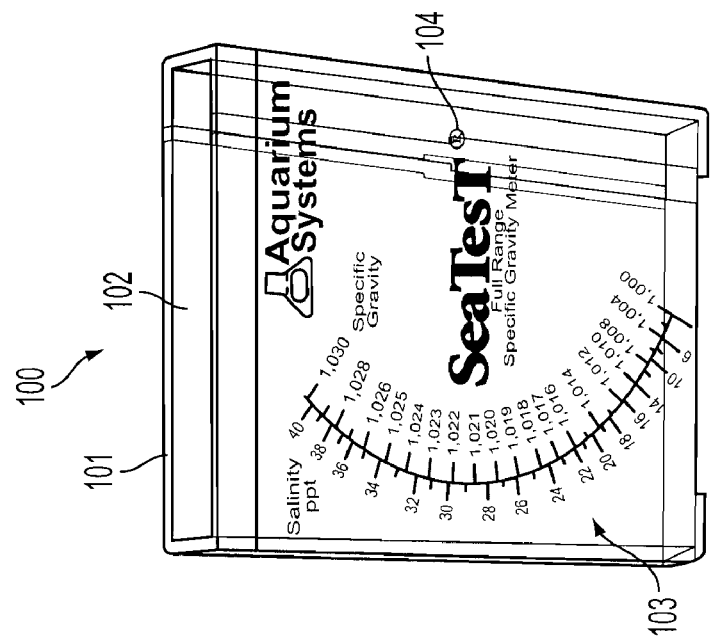
FIG. 2 depicts a perspective view of a hydrometer according to the related art.

Various embodiments of the invention are discussed in detail below. While specific embodiments are discussed, specific terminology is employed for the sake of clarity. However, the invention is not intended to be limited to the specific terminology so selected and it should be understood that this is done for illustration purposes only. A person skilled in the relevant art will recognize that other components and configurations can be used without parting from the spirit and scope of the invention. Each specific element includes all technical equivalents that operate in a similar manner to accomplish a similar purpose.

In the following description of certain embodiments of the invention, directional words such as "top," "bottom," "upwardly," and "downwardly" are employed by way of description and not limitation with respect to the orientation of the apparatus and its various components as illustrated in the drawings. Similarly, directional words such as "axial" and "radial" are also employed by way of description and not limitation.

Figure 1:
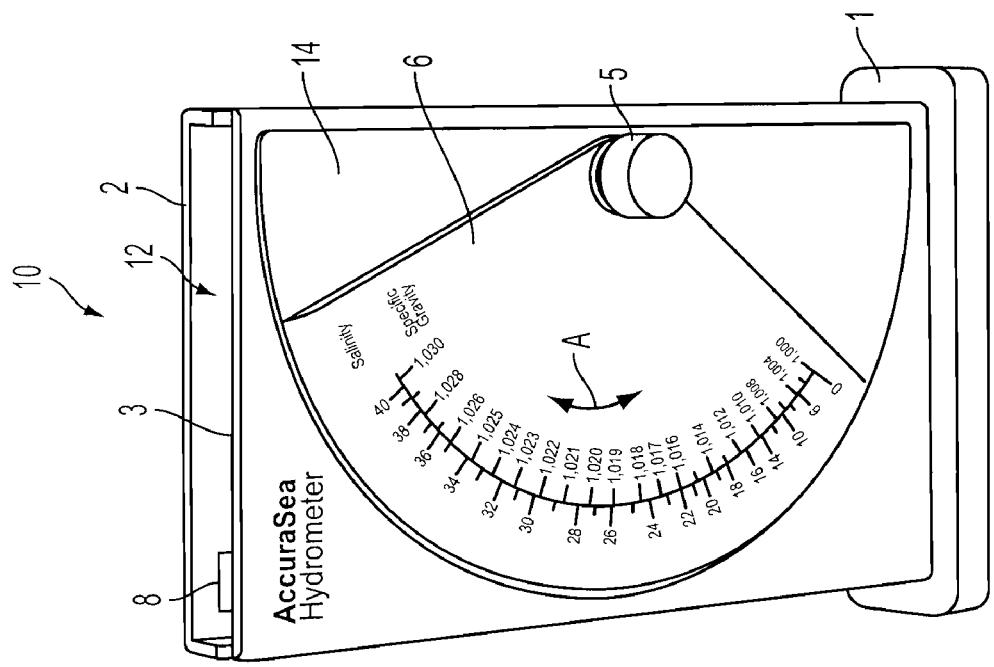
FIG. 1 depicts a perspective view of a hydrometer according to an example embodiment of the invention.

FIG. 1 depicts a perspective view of a hydrometer 10 according to an example embodiment of the invention. FIG. 2 depicts a perspective view of a hydrometer 100 according to the related art. The hydrometer 100 of FIG. 2 may include a container 101 made, for example, of plastic material, and having an opening 102 at a top end thereof. A specific gravity scale 103 may be imprinted in a fixed position on a wall of the container 101. A pivotable floating indicator (not shown) may be disposed within the container 101 and arranged to pivot about an axis point 104 when the container 101 is filled with a liquid, the specific gravity and/or salinity of which is to be measured.

Referring again to FIG. 1, the hydrometer 10 may include a first (back) wall portion 2 coupled to a second (front) wall portion 3 to define a container or box structure constructed to contain a liquid, the specific gravity and/or salinity of which is to be measured. The box structure of the hydrometer 10 may have a closed bottom and an opening 12 at an end opposite the closed bottom. The first (back) wall portion 2 may include a port or fill hole 8 disposed substantially adjacent to the opening 12 on a back or side wall and may allow the liquid to fill the box structure. The fill hole or port 8 on the first (back) wall portion 2 may serve to set a fill line (i.e., the liquid overflows at the bottom of the port) and it may further serve as a liquid inlet when filling the box structure. For example, a user may dip the hydrometer 10 a sufficient depth into the liquid to be measured such that the liquid may flow into the container via the port 8.

The second (front) wall portion 3 may include a recessed or embossed portion 14 in the shape of, for example, a half circle and dimensioned to receive a dial member (plate) 6 such that the dial member 6 is moveable or pivotable therein. The dial member 6 may be in the shape of, for example but not limited to, a pie piece (e.g., an arched/curvilinear edge bounded by two straight edges which come together at an angle opposite the arched/curvilinear edge) and may be pivotably attached within the recessed portion 14. Dial member 6 may, for example, be adapted to pivot as shown by direction arrow A. A knob member 5 (tightening device) may be disposed on an outer surface of the second (front) wall portion 3 and may be selectively rotated by a user to stop and securely prevent movement of the dial member 6 within the recessed portion 14 to calibrate the hydrometer 10. The hydrometer 10 as shown in the embodiment of FIG. 1 will be discussed in further detail below with reference to FIGS. 3-11.

Figure 3:
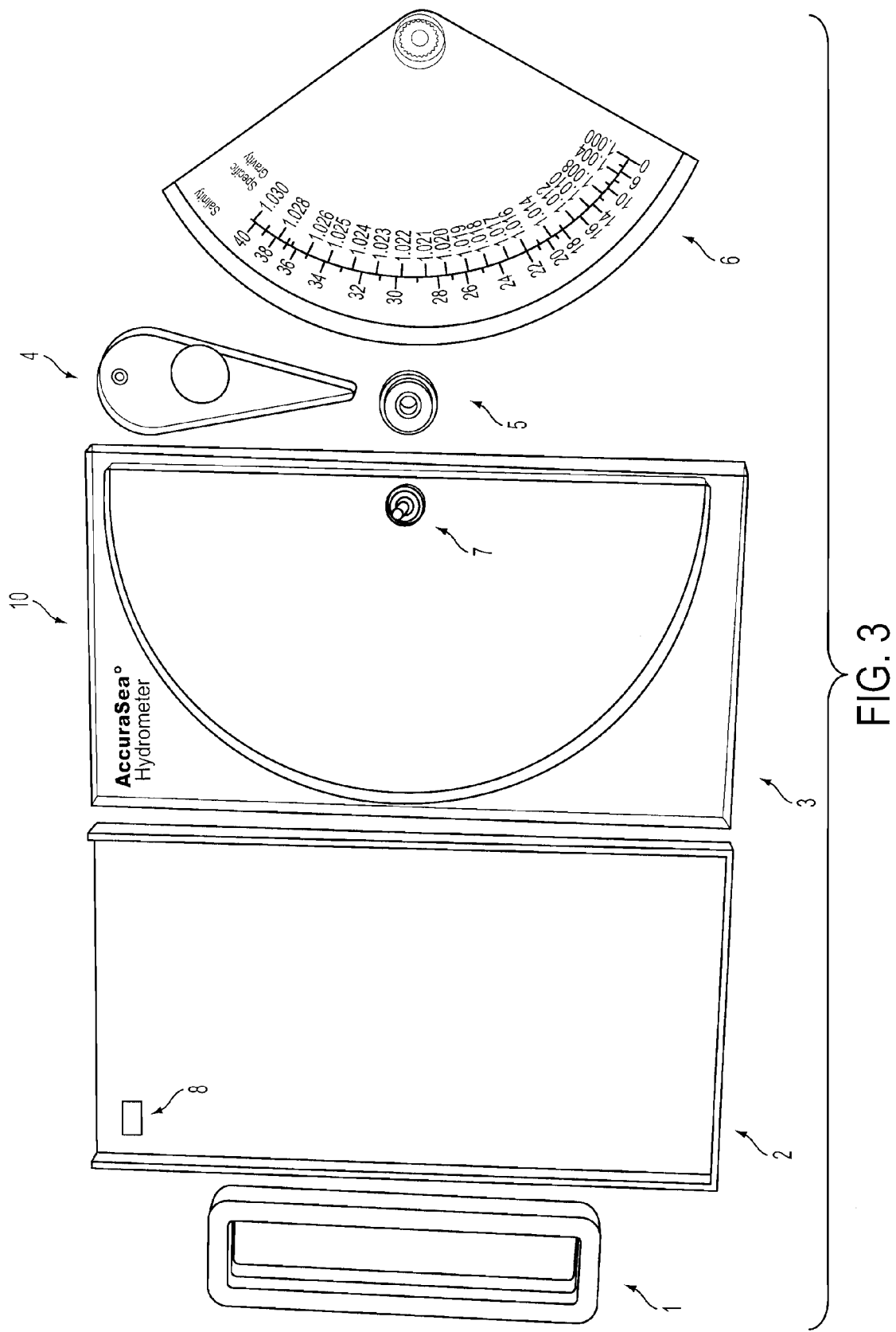
FIG. 3 depicts a disassembled view of the hydrometer of FIG. 1.

FIG. 3 depicts a disassembled view of the hydrometer 10 of FIG. 1. A base member 1 may be constructed to receive the box structure formed from the first (back) wall portion 2 and the second (front) wall portion 3. The base member 1 may be used to stabilize the assembly so that it does not tip easily when stored or when set on a surface to read a measurement provided by the hydrometer 10. The base member 1 may be a separate piece or may be formed as an integrally molded part of one or both of the first and second wall portions 2, 3. A buoyant indictor member (pointer) 4 is shown and may be disposed within the box structure of the hydrometer 10. The buoyant indicator member 4 may be a conventional indicator member used in known box-type, swing-arm hydrometers and may be supplied by a third party. The buoyant indicator member 4 may be, for example, a molded plastic part and may comprise a special weighted member (e.g., a round disc) that has a proprietary composition set into the pointer for temperature compensation.

The knob member 5 is also shown in FIG. 3. The knob 5 may have an internally threaded insert 34 (see FIGS. 8 and 9) configured to receive an externally threaded screw insert 7 which is fixedly received in a boss 16 in the recessed portion 14 of the second (front) wall portion 3. FIG. 3 also shows the dial member 6 which includes a hole 32 (see FIG. 7) constructed to receive the screw insert 7.

Figure 4:
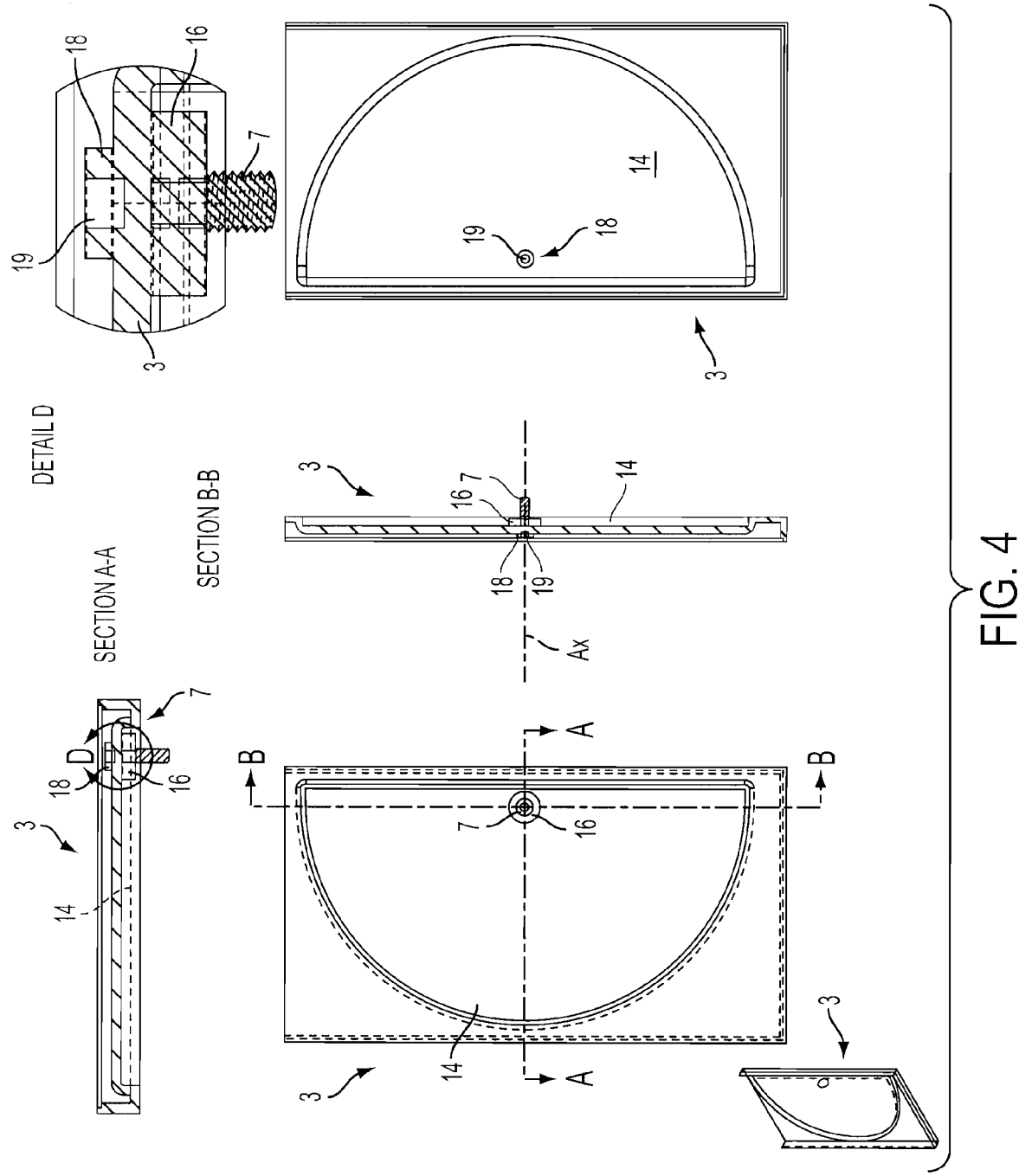
FIG. 4 depicts several views of a front portion of the box structure of the hydrometer of FIGS. 1 and 3.

FIG. 4 depicts several views of the second (front) wall portion 3 of the box structure of the hydrometer 10. The second (front) wall portion 3 may be constructed of transparent plastic material such as, for example, clear high impact polystyrene (HIPS). As described above, although the recessed portion 14 may be shaped like a half circle, other shapes may also be appropriate depending upon the size of the box structure and the shape of the dial member 6. The recessed portion 14 may include the boss 16 which fixedly receives the insert screw 7. The insert screw 7 may be, for example, molded or otherwise fixedly received in the boss 16. The dial member 6 may be received in the recessed portion 14 whereby a hole 32 in the dial member 6 receives the insert screw 7 and a circular recess 33 of the dial member receives the boss 16. When the knob member 5 is loosened, the dial member 6 may be freely movable within the recessed portion by simply pushing it in one direction or the other about the axis Ax.

Since the weight of the dial member 6 acts as a lever about axis Ax, the contact interface between the circular recess 33 and the boss 16 may be sized as necessary to prevent movement of the dial member 6 due to its own weight when the dial member 6 is tightened sufficiently. The weight of the dial member 6 may also be counteracted by inserting, for example, rubber or other friction providing devices in the contact interface between the circular recess 33 and boss 16. The knob member 5 may also be provided with a wider base to allow sufficient tightening to hold the dial member 6 in position once calibrated.

Figure 6:
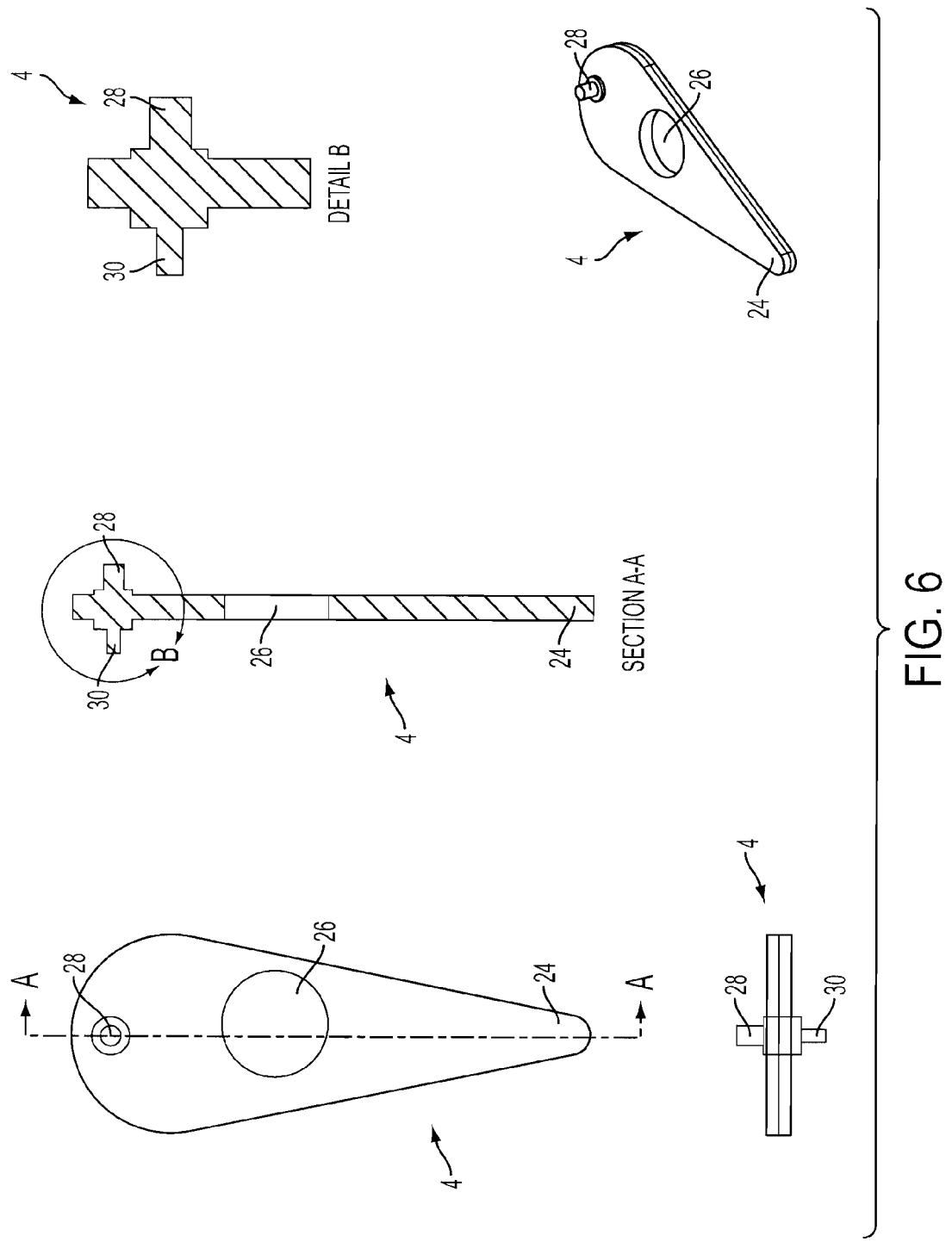
FIG. 6 depicts several views of a buoyant indicator member of the hydrometer of FIGS. 1 and 3.

On an opposite side of the second (front) wall portion 3 another boss 18 is provided and may include a blind hole 19 for receiving a first post or shaft 28 of the buoyant indicator member 4 so that the buoyant indicator member 4 can pivot (see FIG. 6). The threaded insert 34 of the knob 5 may be threadedly attached to the screw insert 7 and may be tightened to allow a user to use the knob to selectively stop the dial member 6 at any position within the recessed portion 14 to calibrate the hydrometer 10.

Figure 5:
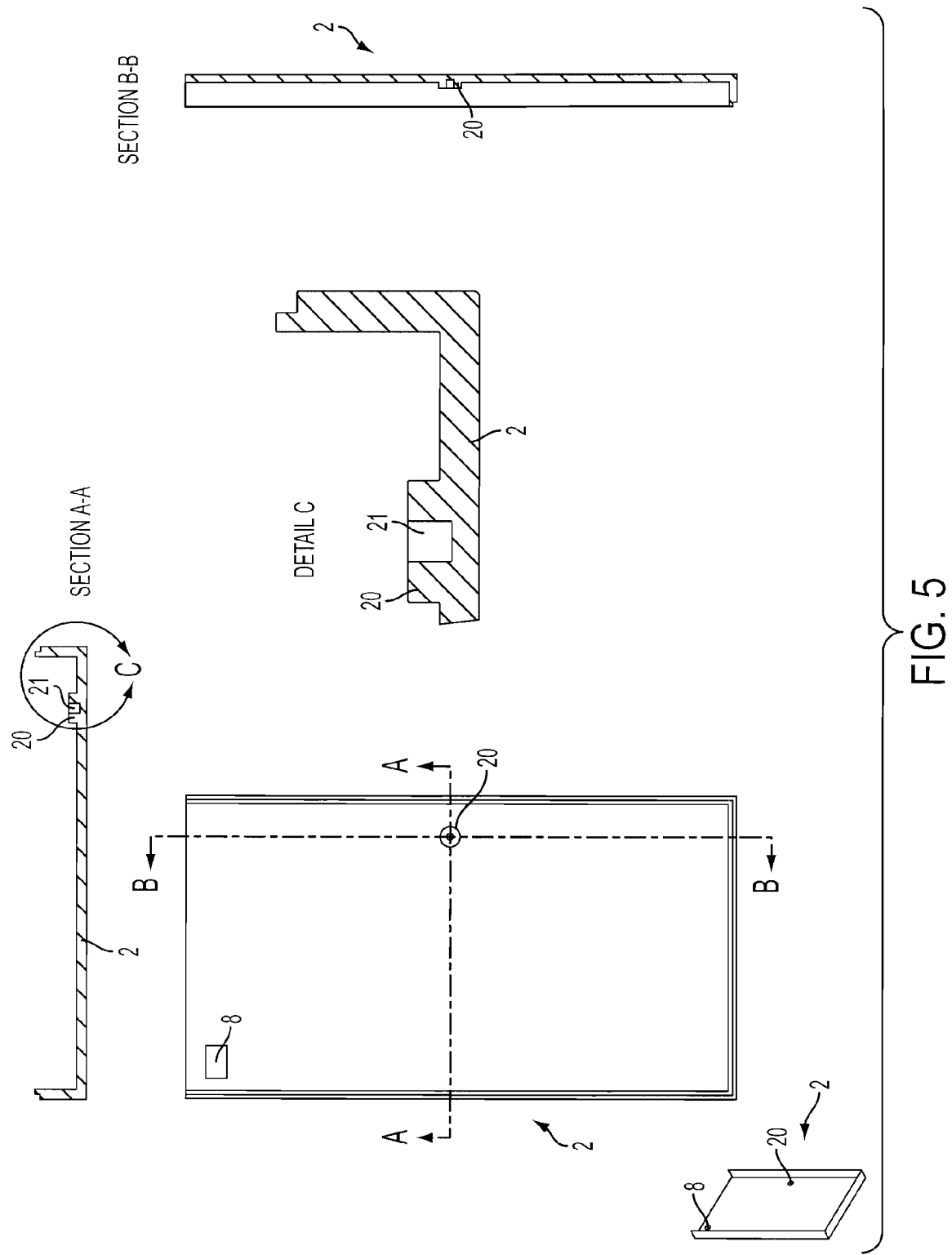
FIG. 5 depicts several views of a back portion of the box structure of the hydrometer of FIGS. 1 and 3.

FIG. 5 depicts several views of the first (back) wall portion 2 of the box structure of the hydrometer 10. The first (back) wall portion 3 may be constructed of non-transparent plastic material such as, for example, transparent, white, or other colored high impact polystyrene (HIPS). Other similar materials could also be used. As described above, the wall portion 2 may include the port or fill hole 8 at an end disposed opposite the bottom. The port 8 may serve two purposes: it may allow filling of the box structure with a minimum formation of bubbles and it may set the liquid fill level. Although the port 8 is shown in FIGS. 1, 3, and 5 on a back wall of the wall portion 2, the port 8 may be moved to a side of the body to avoid it interfering with the reading of the specific gravity scale on the dial member 6 and/or any product identity printed on the second (front) wall portion 3. The wall portion 2 may also include a boss 20 having a blind hole 21 which, when the box structure is assembled, may be positioned opposite the boss 18 and blind hole 19 of the second (front) wall portion 3 such that posts 28, 30 of the buoyant indicator member 4 (see FIG. 6) may be pivotably received in the holes 19, 21, respectively.

FIG. 6 depicts several views of the buoyant indicator member (pointer) 4 of the hydrometer 10. The pointer 4 may include a tapered or pointed end 24 for indicating the specific gravity and/or salinity of a liquid on the scale imprinted on the dial member 6. The pointer 4 may also include a first post 28 and a second post 30 which may be rotatably received within the holes 19 and 21 of the first and second wall portions 2, 3, respectively. The pointer may be formed from a plastic material such as, for example, polypropylene (PP) or another similar material and may include a hole 26 within which a special weighted member (e.g., a round disc) may be disposed. The weighted member may have a proprietary composition as one of ordinary skill in the art will recognize.

Figure 7:
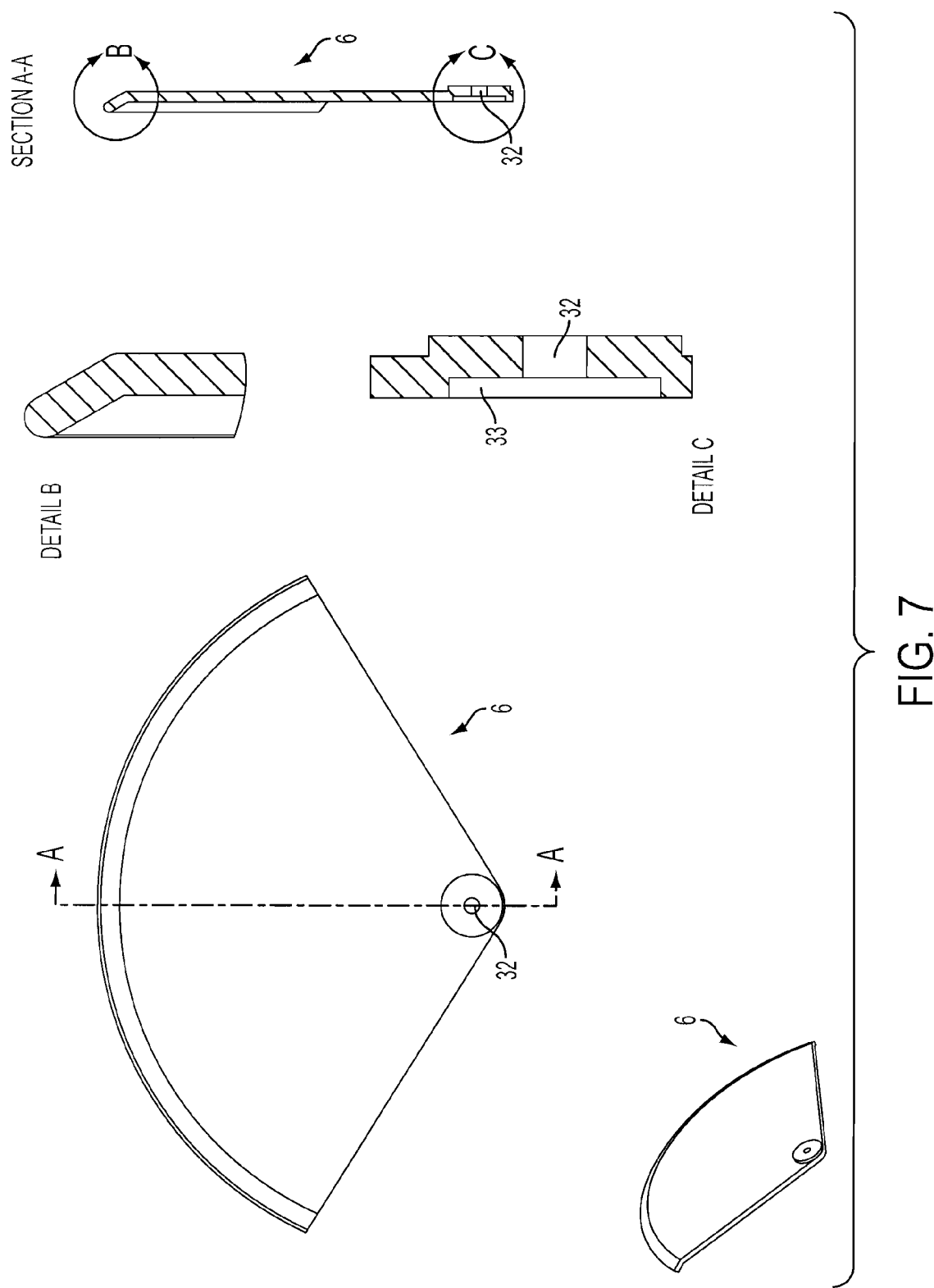
FIG. 7 depicts several views of a dial member (plate) of the hydrometer of FIGS. 1 and 3.

FIG. 7 depicts several views of the dial member (plate) 6 of the hydrometer 10. The dial member 6 may be in the shape of, for example but not limited to, a pie piece (e.g., an arched/curvilinear edge bounded by two straight edges which come together at an angle opposite the arched/curvilinear edge) and may be pivotably attached within the recessed portion 14 of the second (front) wall portion 3. The dial member 6 may include the hole 32 and the circular recess 33. The insert screw 7 of the second (front) wall portion 3 may be fixedly received, e.g., molded or glued, within the hole 32 and the boss 16 may be received in the circular recess 33.

Figure 8:
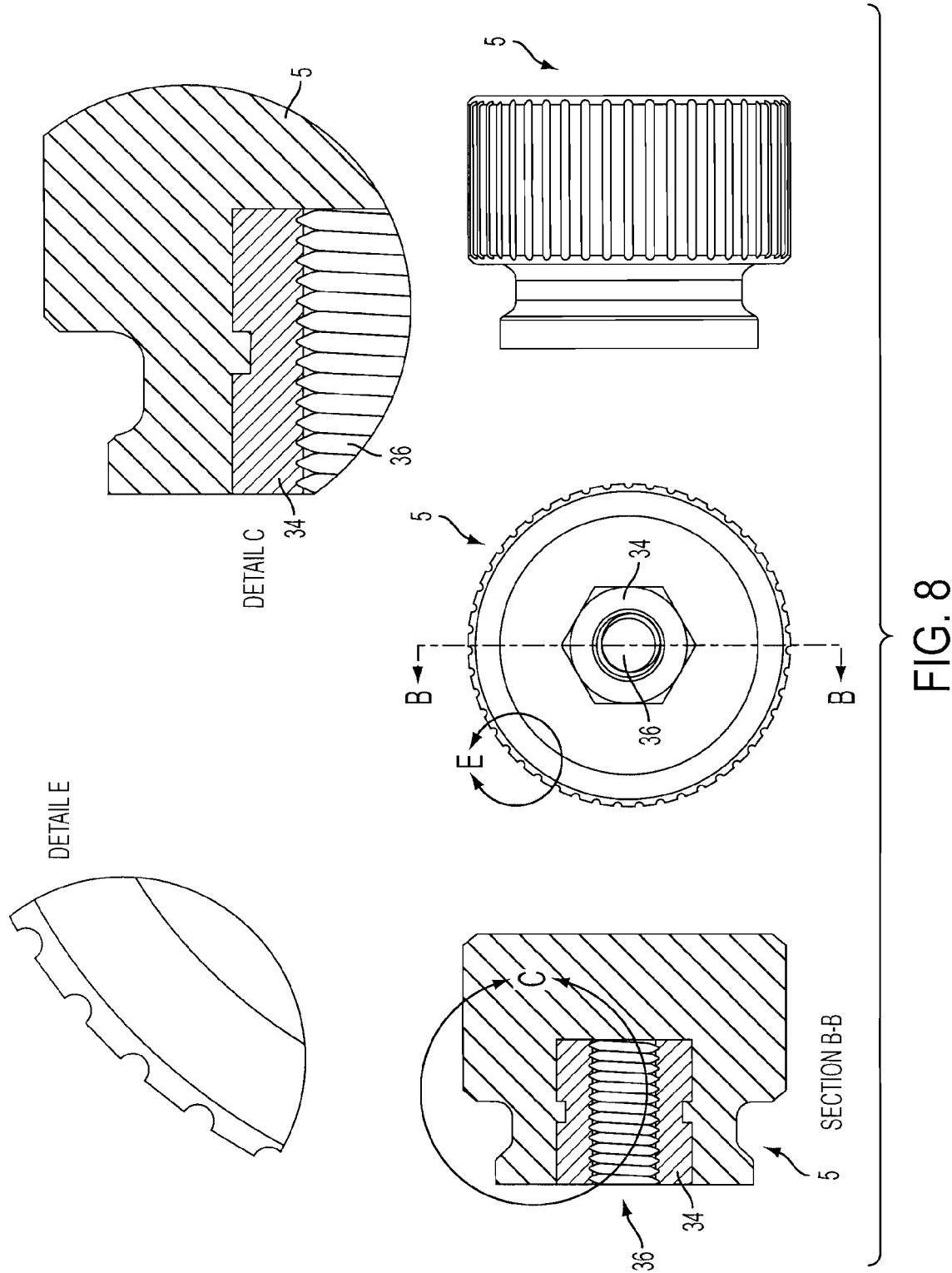
FIG. 8 depicts several views of a knob assembly of the hydrometer of FIGS. 1 and 3.
Figure 9:
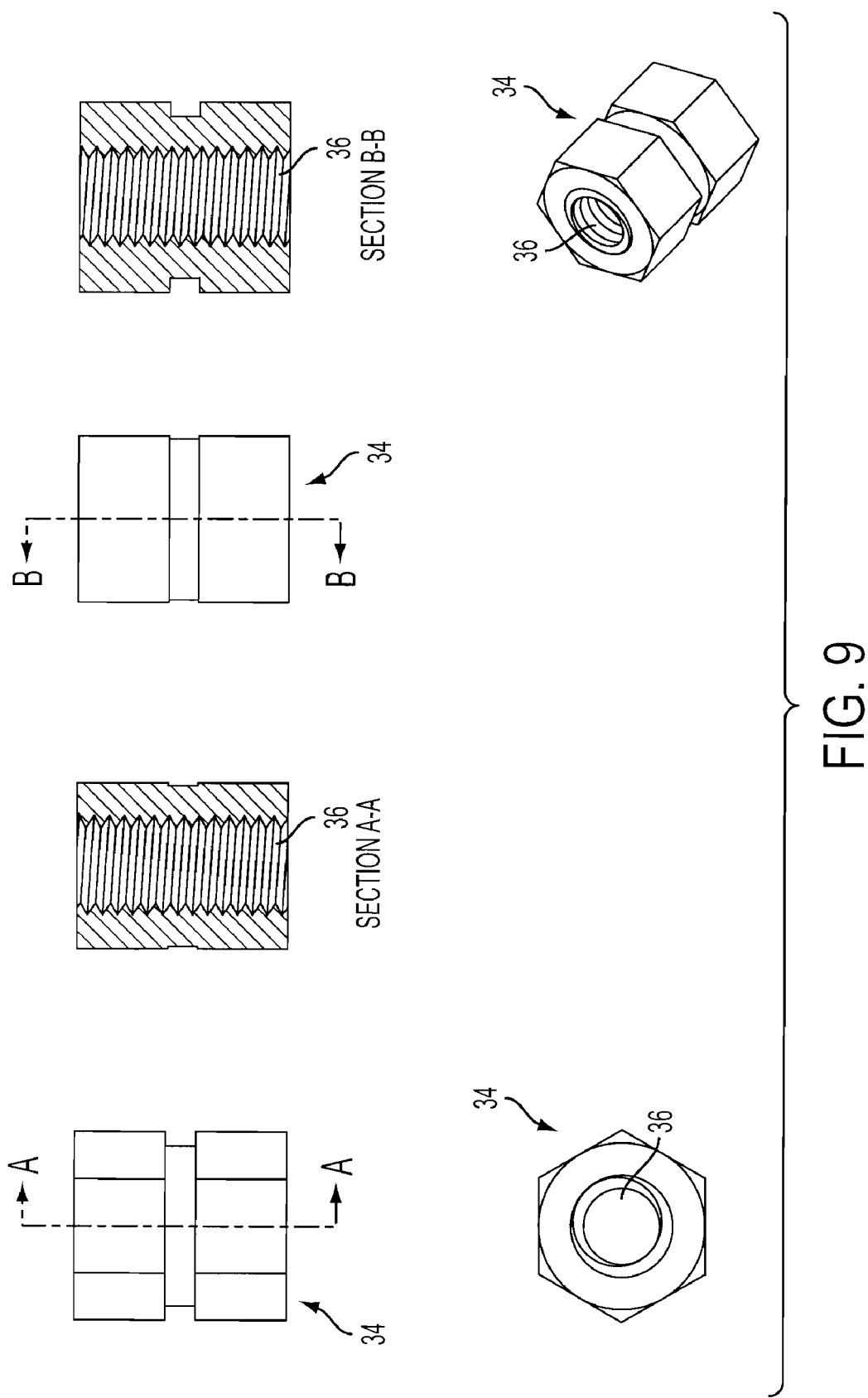
FIG. 9 depicts several views of a knob insert of the hydrometer of FIGS. 1 and 3.

FIG. 8 depicts several views of the knob assembly 5 of the hydrometer 10. FIG. 9 depicts several views of a knob insert member 34 of the hydrometer 10. The knob 5 may be a molded plastic part within which an internally threaded insert member 34 is disposed. The insert member 34 may have a threaded hole 36 therethrough and may have a hexagonal shape to prevent rotation of the insert member 34 within the knob 5. The insert member 34 may be formed from a metal material such as, for example, stainless steel. The molded plastic body of the knob 5 may be formed from a plastic material such as, for example, high impact polystyrene (HIPS).

Figure 10:
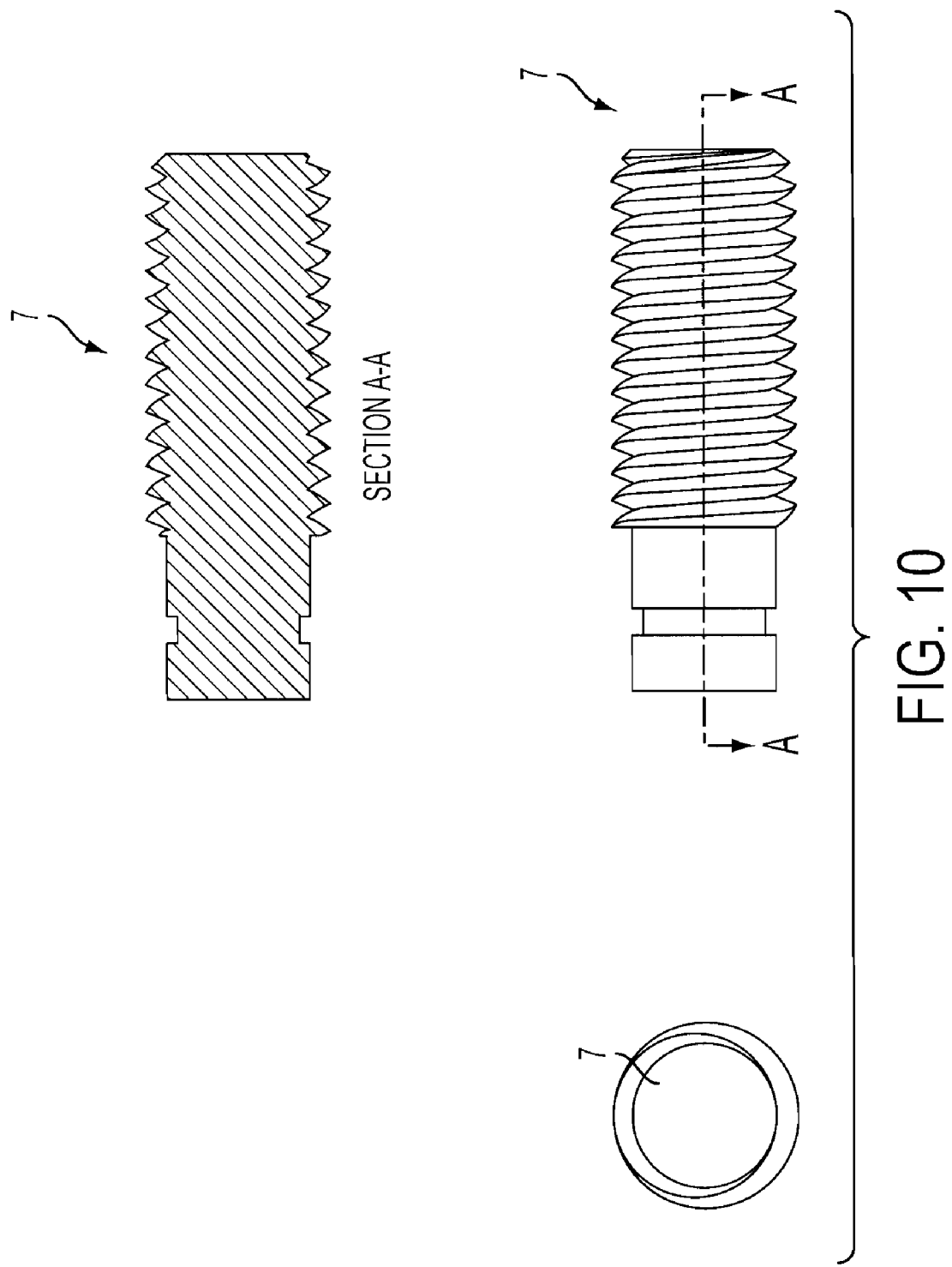
FIG. 10 depicts several views of a screw insert member of the hydrometer of FIGS. 1 and 3.

FIG. 10 depicts several views of the screw insert member 7 of the second (front) wall portion 3 of the hydrometer 10. The screw insert member 7 may be threaded along at least a portion of its length so as to be received by the internal threads of the knob insert member 34. The screw insert member 7 may also have a non-threaded portion along its length which may be, for example, molded or glued into the boss 16 of the second (front) wall portion 3. The screw insert member 7 may be made from, for example, high quality stainless steel, so as to limit the possibility of corrosion, but may also be made from a suitably strong alternative material that can resist the damaging effects of saltwater.

Figure 11:
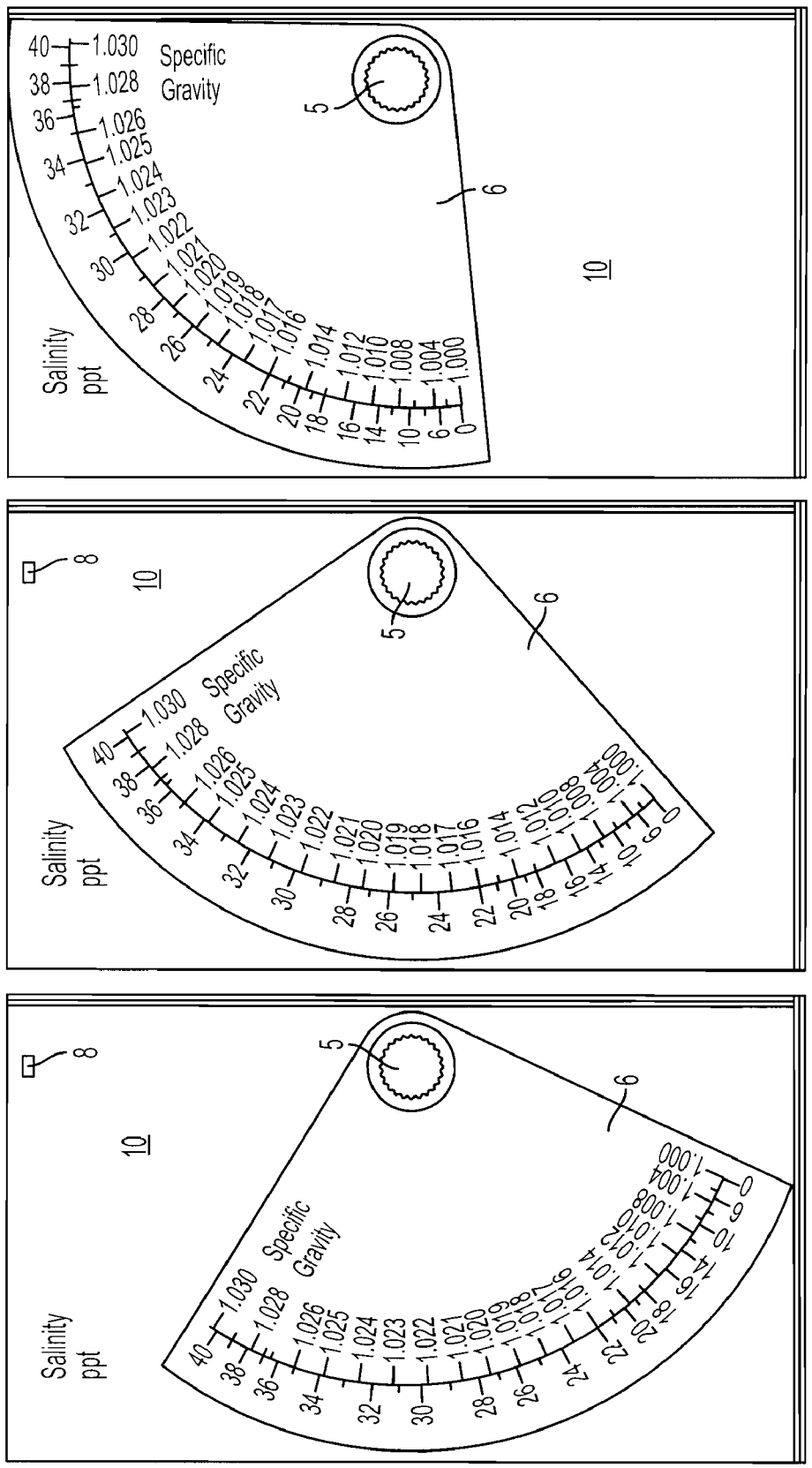
FIG. 11 depicts several front views of a hydrometer showing an adjustable dial member in several different positions relative to the box structure according to an embodiment of the invention.
Figure 12A:
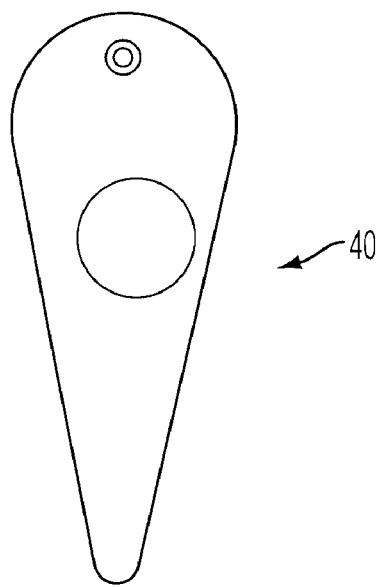
FIGS. 12a-d depict top, side, rear, and perspective views, respectively, of a pointer or indicator member for a hydrometer according to an embodiment of the invention.
Figure 12B:
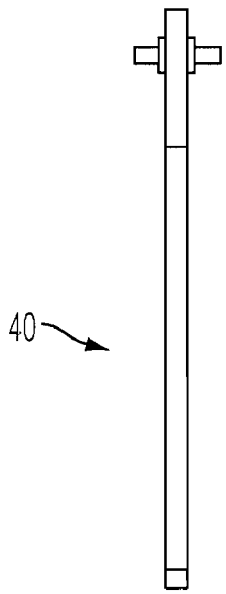
Figure 12C:
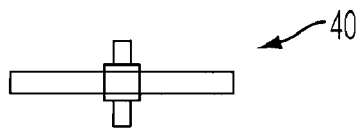
Figure 12D:
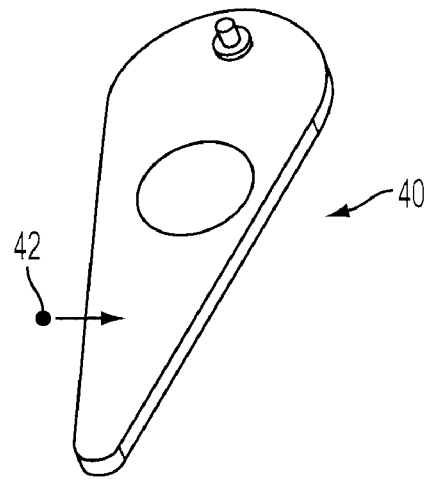

FIG. 11 depicts several front views of the hydrometer 10 showing the adjustable dial member 6 in several different positions relative to the box structure. In the embodiment shown in FIG. 1, the movable dial member 6 may have specific gravity and salinity or, alternatively, density and salinity scales, silkscreened or molded thereon. Two separate dials (not shown) may be provided—one for American users who are familiar with the measurements in salinity and specific gravity, and the other dial being for European users who are familiar with the measurements in salinity and density. These scales are slightly different as one of skill in the art will recognize.

In use, the hydrometer 10 may solve accuracy problems common in known box-style, swing arm hydrometers by making it possible for the user to calibrate the hydrometer by adjusting the position of the dial member based on a reference solution having predetermined salinity and specific gravity values. For example, when a user is ready to test the salinity and/or specific gravity of natural or artificial seawater, the user can first fill the box structure of the hydrometer 10 with the reference solution. The buoyant indicator member 4 will pivot based on the specific gravity of the reference solution. The user can rotate the dial member 6 as necessary so that the scale and the indicator member 4 indicate the correct salinity/density or salinity/specific gravity of the solution. Then by tightening the knob 5, the user can fix the position of the dial member 6. Now that the hydrometer 10 is calibrated, the hydrometer 10 can be emptied and refilled through the port or fill hole 8 with the natural or artificial seawater to be tested. The hydrometer 10 should provide a correct reading of the salinity and/or specific gravity of the natural or artificial seawater. As one of ordinary skill will recognize, the indicator member 4 may be capable of "temperature compensating," i.e., it may be calibrated to work within a certain temperature range and may be made of a plastic that changes with temperature in a manner consistent with, for example, seawater.

In another embodiment (not shown) of the hydrometer, the salinity and/or specific gravity scale may also be adjustable for purposes of calibration by being provided on a removable sticker or label which can be attached to the face of the second (front) wall portion 3. The scale may then be moved as necessary based on the position of the pointer in the reference solution.

The dial member 6 shown in the above embodiment is described as being pie-shaped. It may also be possible to make the dial member any number of different shapes. For example, it may be possible to design a hydrometer with a wider box, or a differently shaped central area, and make the dial member circular, such that the knob and the pivot position for the pointer (e.g., indicator member 4) may be disposed in the center of the container.

FIGS. 12a-d depict top, side, rear, and perspective views, respectively, of a pointer or indicator member 40 for a hydrometer according to another embodiment of the invention. As an alternative to, or in conjunction with, calibration of a hydrometer using the movable/adjustable dial member 6 described above, a user may also be able to calibrate the hydrometer by altering the buoyancy of the pointer or indicator member which floats freely inside the hydrometer. For example, the user could add or subtract a small amount of weight from the pointer 40 to calibrate the hydrometer. This may be accomplished with adhesive labels of very small size such as, for example, in the form of weighted or buoyant adhesive dots 42 (see FIG. 12d) which affects its buoyancy and thus the position where it rests in a sample of water during measurement. The dots 42 may be made from any type of material that is either buoyant in water (to subtract weight from the pointer) or sinks in water (to add weight to the pointer). For purposes of applying the dots 42 during calibration, the pointer may be removable from the hydrometer housing (not shown). As in the embodiment discussed previously, the pointer may be formed from a plastic material such as, for example, polypropylene (PP) or another similar material and may include a hole within which a special weighted member (e.g., a round disc) may be disposed. The weighted member may have a proprietary composition as one of ordinary skill in the art will recognize. According to this embodiment, the hydrometer scale (not shown) may be fixed or moveable relative to the hydrometer housing as described above. That is, the hydrometer may have both a scale on a moving dial (or otherwise moveable relative to the box structure) and/or a removable, weight adjustable pointer for purposes of calibration.

In another embodiment of the invention (not shown), a hydrometer may be provided without an integrated box structure and including only a buoyant indicator member (pointer) pivotably disposed about an axis on a support structure having a salinity/density or salinity/specific gravity scale. Such a "boxless" hydrometer may be calibrated using at least one adhesive member adapted to be removably adhered to the pointer by a user so that the hydrometer can be calibrated based on a reference solution having a predetermined salinity. The at least one adhesive member may be configured to increase or decrease the buoyancy of the pointer. A transparent box structure with a reference solution having a predetermined salinity may be provided and the hydrometer may be inserted by a user to take a reading. The user may then calibrate the hydrometer by moving a movable dial member having the scale and/or adhering the at least one adhesive member to the indicator member (pointer) as necessary such that the indicator member indicates the predetermined salinity of the reference solution on the scale. The reference solution may be removed from the box structure so that it can be filled with the liquid to be measured or, alternatively, the "boxless" hydrometer may be inserted the support structure into an aquarium for taking measurements. The salinity/density or the salinity/specific gravity of the liquid may then be measured by reading the salinity/density or the salinity/specific gravity indicated on the scale by the buoyant indicator member.

In another embodiment of the invention (not shown), a box or support structure such as, for example, those described herein, may include a level indicating device to allow the user to confirm the hydrometer is level when readings are taken. This device may be, for example, a pair of liquid-filled cylinders with indicator bubbles. The level indicating device may be, for example, a level line printed on the box. This is important because the position where the pointer comes to rest is influenced by gravity and thus the angle of the box and/or support for the pointer.

In another embodiment of the invention (not shown), the box structure may include a plunger or piston that allows the user to draw water into the box structure without producing bubbles.

The potential applications of the hydrometer are not limited to measurement of the salinity of brackish and marine water. Hydrometers are also used in measurement of density of other liquids, for example but not limited to, in beer making and for batteries. The embodiments of the hydrometer described herein could have use for measurement of density in other industries.

While various embodiments of the present invention have been described above, it should be understood that they have been presented by way of example only, and not limitation. Thus, the breadth and scope of the present invention should not be limited by any of the above-described embodiments, but should instead be defined only in accordance with the following claims and their equivalents.

The invention claimed is:

1. A hydrometer comprising:
 a box structure comprising side walls and a bottom, wherein at least a portion of one of the side walls is substantially transparent;
 a buoyant indicator member pivotably disposed about an axis within the box structure, wherein the indicator member pivots about the axis when the box structure is filled with a liquid;
 a salinity/density scale or salinity/specific gravity scale disposed on a surface of the box structure or a dial member; and
 at least one adhesive member adapted to be removably adhered to the indicator member by a user so that the hydrometer can be calibrated based on a reference solution having a predetermined salinity, wherein the at least one adhesive member increases or decreases the buoyancy of the indicator member.

2. The hydrometer according to claim 1, wherein the buoyant indicator member is removable.

3. The hydrometer according to claim 1, wherein the salinity/density scale or salinity/specific gravity scale is adjustable relative to the box structure.

4. The hydrometer according to claim 1, wherein the salinity/density scale or salinity/specific gravity scale is fixed relative to the box structure 5. A kit comprising:
 a container containing a reference solution having a predetermined salinity; and
 a hydrometer including:
  a box structure comprising side walls and a bottom, wherein at least a portion of one of the side walls is substantially transparent;
  a buoyant indicator member pivotably disposed about an axis within the box structure, wherein the indicator member pivots about the axis when the box structure is filled with a liquid;
  a salinity/density or salinity/specific gravity scale disposed on a surface of the box structure or a dial member; and
  at least one adhesive member adapted to be removably adhered to the indicator member by a user so that the hydrometer can be calibrated based on the reference solution having a predetermined salinity, wherein the at least one adhesive member increases or decreases the buoyancy of the indicator member.

6. The kit according to claim 5, wherein the buoyant indicator member is removable.

7. The kit according to claim 5, wherein the salinity/density scale or salinity/specific gravity scale is adjustable relative to the box structure.

8. The kit according to claim 5, wherein the salinity/density scale or salinity/specific gravity scale is fixed relative to the box structure.

9. A hydrometer comprising:
 means for containing a liquid; and
 means for indicating the salinity/density or the salinity/specific gravity of the liquid contained in said liquid containing means, wherein said indicating means is adjustable relative to the liquid containing means so that the hydrometer can be calibrated based on a reference solution having a predetermined salinity.

10. A kit comprising:
 the hydrometer of claim 9; and
 a container containing the reference solution having a predetermined salinity.

11. A method of measuring the salinity/density or the salinity/specific gravity of a liquid, the method comprising:
 providing a hydrometer comprising:
  a box structure comprising side walls and a bottom, wherein at least a portion of one of the side walls is substantially transparent;
  a buoyant indicator member pivotably disposed about an axis within the box structure; and
  a salinity/density or salinity/specific gravity scale disposed on a surface of the box structure or a dial member;
 providing at least one adhesive member adapted to be removably adhered to the indicator member by a user so that the hydrometer can be calibrated based on a reference solution having a predetermined salinity, wherein the at least one adhesive member is configured to increase or decrease the buoyancy of the indicator member;
 filling the hydrometer with a reference solution having a predetermined salinity;
 calibrating the hydrometer by adhering the at least one adhesive member to the indicator member as necessary such that the indicator member indicates the predetermined salinity of the reference solution on the scale;
 removing the reference solution from the box structure;
 filling the calibrated hydrometer with the liquid to be measured; and
 measuring the salinity/density or the salinity/specific gravity of the liquid by reading the salinity/density or the salinity/specific gravity indicated on the scale by the buoyant indicator member.

* * * * *